US007592506B2

(12) United States Patent
Grotewold et al.

(10) Patent No.: US 7,592,506 B2
(45) Date of Patent: Sep. 22, 2009

(54) TRANSGENIC PLANTS WITH ALTERED LEVELS OF PHENOLIC COMPOUNDS

(75) Inventors: Erich Grotewold, Columbus, OH (US); Anusha P Dia, Columbus, OH (US); Edward L. Braun, Gainesville, FL (US)

(73) Assignee: The Ohio State University Research Foundation, Columbus, OH (US)

( * ) Notice: Subject to any disclaimer, the term of this patent is extended or adjusted under 35 U.S.C. 154(b) by 455 days.

(21) Appl. No.: 11/615,494

(22) Filed: Dec. 22, 2006

(65) Prior Publication Data

US 2008/0235829 A1 Sep. 25, 2008

Related U.S. Application Data

(62) Division of application No. 10/093,837, filed on Mar. 8, 2002, now Pat. No. 7,154,023.

(60) Provisional application No. 60/274,629, filed on Mar. 8, 2001.

(51) Int. Cl.
*C12N 15/29* (2006.01)
*C12N 15/82* (2006.01)
*A01H 5/00* (2006.01)

(52) U.S. Cl. .................. 800/286; 800/285; 800/298; 536/23.1

(58) Field of Classification Search ............... None
See application file for complete search history.

(56) References Cited

U.S. PATENT DOCUMENTS

| 5,773,697 | A | 6/1998 | Tomes et al. |
| 5,955,361 | A | 9/1999 | Li et al. |
| 6,127,602 | A | 10/2000 | Nichols |
| 6,156,956 | A | 12/2000 | Theologis et al. |
| 6,177,614 | B1 | 1/2001 | Colasanti et al. |
| 7,154,023 | B2 | 12/2006 | Grotewold et al. |

OTHER PUBLICATIONS

Rabinowicz et al. Genetics, vol. 153, Sep. 1999, pp. 427-444.*
Notice of Allowance from U.S. Appl. No. 10/093,837 mailed Jul. 31, 2006.
Notice of Allowance from U.S. Appl. No. 10/093,837 mailed Apr. 25, 2006.
Office Action from U.S. Appl. No. 10/093,837 mailed Mar. 30, 2005.
Office Action from U.S. Appl. No. 10/093,837 mailed Aug. 6, 2004.
Braun et al, "Transcription Factors and Metabolic Engineering: Novel Applications for Ancient Tools", Regulation of Phytochemicals by Molecular Techniques, vol. 35.
Dias et al., "Metabolite Profiling as a Functional Genomics Tool", Methods in Molecular Biology (undated), vol. 236, pp. 415-425, published Sep. 1, 2001.
Dias et al., "Metabolite Profiling as a Functional Genomics Tool", 4th Annual Plant Molecular Biology and Biotechnology Research Symposium, The Ohio State University, Mar. 2, 2002.

Dias et al., "Metabolite Profiling as a Functional Genomics Tool", The Ohio State University, Hayes Research Forum, Mar. 2, 2002, slides.
Dias et al., "Duplication and Functional Divergence of R2R3 Myb Regulatory Genes in the Grasses", 44th Annual Maize Genetics Conference, Programs and Abstracts, Mar. 14-17, 2002, p. 25.
Dias et al., "Recently Duplicated Maize R2R3 Myb Genes provide evidence for distinct mechanisms of evolutionary divergence after duplication", Plant physiology, Feb. 2003, vol. 131, pp. 610-620.
Dias et al., "Manipulating the accumulation of phenolics in Maize cultured cells using transcription factors", Biochemical Engineering Journal, 2003, pp. 207-216.
Friedman et al., "Expression of Truncated Viral Trans-activator Selectively Impedes Lytic Infection by its Cognate Virus", Nature, Sep. 1988, vol. 33, pp. 452-454.
Genbank Accession No. AF099394, Nov. 9, 1999.
Guyer et al. "Activation of Latent Transgenes in *Arabidopsis* Using a Hybrid Transcription Factor", Genetics, Jun. 1998, vol. 149, pp. 633-639.
Heilmann et al., "New medical applications of plant secondary metabolites", Functions of Plant Secondary metabolites, M Wink, Boca Raton, CRC Press LLC, 3: 274-310, 1999.
Hiratsu et al., "Dominant Repression of Target Genes by Chimeric Repressors that include EAR motif, a Repression Domain in *Arabidopis*", The Plant Journal, 2003, vol. 34, pp. 733-739.
Mehrtens et al., "The *Arbidopsis* Transcription 'factor MYB12 is a Floavonol-Specific Regulator of Phenylpropanoid Biosynthesis", Plant Phsysiology, Jun. 2005, vol. 138, pp. 1083-1096.
Millar et al., "The *Arabidopsis* GAMYB-Like Genes, MYB33 and MYB 65, are MicroRNA-Regulated Genes that redundantly facilitate anther development", The Plant Cell, vol. 17, pp. 705-721, Mar. 2005.
Rabinowicz et al., "Maize R2R3 Myb genes: Sequence analysis reveals amplification in higher plants", Genetics, vol. 153, Sep. 1999, pp. 427-444.
Ruden, "Generating Yeast Transcriptional Activators Containing No Yeast Protein Sequence", Nature, vol. 350, Mar. 1991, pp. 250-252.
Tamagnone et al., "The AmMYB308 and AmMYB330 Tanscription Factors from Antirrhinum Regulate phenylpropanoid and Lignin Biosynthesis in Transgenic Tobacco", The Plant Cell, vol. 10, Feb. 1998, pp. 135-154.
Tamagnone et al. "Inhibition of Phenolic Acid Metabolism Results in Precocious Cell Death and Altered Cell Morphology in Leaves of Transgenic Tobacco Plants", The Plant Cell, vol. 10, Nov. 1998, pp. 1801-1816.

* cited by examiner

*Primary Examiner*—Russell Kallis
(74) *Attorney, Agent, or Firm*—Calfee, Halter & Griswold LLP

(57) ABSTRACT

Methods for altering levels in plants of one or more phenolic compounds that are intermediates or final products of the plant phenylpropanoid pathway are provided. One method comprises transforming a plant cell with an expression construct comprising a nucleic acid which encodes a transactivator protein comprising the myb domain of the maize "ZmMyb-IF35" protein and an activation domain. Another method comprises transforming a plant cell with an expression construct comprising a transgene which encodes an antisense ZmMyb-IF35 RNA. The present invention also relates to expression constructs and vectors used in the present methods, transformed plant cells and transgenic plants prepared according to the present methods, and the seeds of such transgenic plants.

7 Claims, 10 Drawing Sheets

Fig. 3A

```
TCGACCCACGCGTCCGCACCAGCAGCAGAGCCCCGAGCAATCCCTTCTCGCCCTTTTCAC
TTTTCAGATCCAGCCAGCCAGCCAGCCATCCCACTCCGCACCGCATTCCTCGCAGTGGCA
GAGCTTGCAGCGGTGGTCTCTTCCCCTTCCTCCTGTCTCCTCCTCGCTCGATCTCCTCTC
CCAAGCAGCGAGAAGCGGATGGGGAGGGCGCCGTGCTGCGAGAAGGTGGGGCTGAAGAAG
GGGAGGTGGACCAAGGAGGAGGACGAGGTCCTGGCGAGGTACATCAAGGAGCACGGGGAA
GGATCGTGGAGGTCACTGCCCAAGAATGCCGGTACGGATCGAAGTGGCGAGTTTGTTATA
TTAGCTAGCTCTGTGTGTTGGCAATAGGGGGCTGAGGCTGGTTTTGCTGGCAGGGCTGC
TGCGGTGCGGGAAGAGCTGCAGGCTGCGGTGGATCAACTACCTGCGGGCGGGTCTCAAGA
GGGGGAACATCTCGGAGGAGGAGGAGGACATGATCATCAAGCTCCACGCCACGCTTGGCA
ACAGGTACCTGTCCATGCCTATCTATCTATCTACTATCTGGCATTCGATTCCTTCAACCT
CGAGCTGCTTGGGCCGTGTCCACAGTCCATCTTTTCTCTTTGATTAATTCCTGCGCTTAA
TCAACTCCATCCATGCTCTGGGCCGCTTCAGGGTTCAGAGTTCTTGCACGGTACGTAGTA
GGGGACGAAAAACCCTGTGCGCTTTATTATGCCACCGACCGACAGTGGCGAATCTAGGT
CCAATTTACTTGATATTTTTTTTTTTCTCTCTCTCTCTCCATCTGGTGCAAAGTGAGAAC
GGGAGGGCATGTGCCAAGAAGCTCTGTTCCCCCCTTCCACTGAAAGAGAAGGAACCAAAA
TCAAATGGCAGAGGAACACGGAGTTGCCAAAACCAGGCCGCGCGTAGATGCCCCTCCCCC
TCCCTTCAATTGTTCATTCAGATAGAGCCTGTTTGACTAGTATGCTATCTTTGTTCCATC
AAAAAAAATATAGATGGTTGAAATGTAGTTTTAGAGACTAGAAGAGGTGCGGAAAAGGTC
GCGGTTTTAGCAATGCCTTCCGGATGTCCAGTTAGTGTCGTGGTGCACCCGCCGTCTTGC
CGGCCGGCTAGGTAGAAACGTGGTCAAGACACATTTCTTTCTAGACGGAGACGGAAGAGG
AGGAAGCCGCCCCCCGTGTGCTTTCATGGACAGGATGGTCGAGCAAGCAAAAACCCTGC
ACACTGGACGGTCACCTTTGTCAATGGCCACTTTTTGTCATGGGCGAGTGAGTGCACGG
TACTTTTCTACGTCCGCCCTCGTTGGCCTCGTGCGCGCACGTAGAATGTGCCGCCATCGC
CATGGAAAAGAAGAGGGCAGCCGCAGCGCAGGGAATTATTTCTTCGGTTTCTCTTTCCTC
CGCGCCTCAATCGTTGGTCATTCCCATTGGCGGATTAAAAACAATCCTAAGGGCTAGTTT
AGAAACCTCGTTTTCCCATGAGATTTTTATTTTTTAAGGAAAATTATTCATTTTCTCTT
ATAAAAATAGGAATCCCTTAGAAAAATAGTGTTCCCAAAACACTATTTTCTAAGGGTTTT
TCGTTTTTCCAAGATAAATTAGTTCATTTTTTTGAAAAATTGGAAATTTCATGGAAAAA
TGGTGTTGGCAAACTAGTCCTAAATCTGCAACTTTAATAATCCTTCGTTCTGTCATTATT
AGTACCCCTACTCGTTTTAGCTCTGTTTTTTTTAATTTGAGATATAGACATAAAAAGAA
CCTAAATTCAGACGTCTAAACAAATTTTACCGAGTTGCAAAATGAATGAATCAGGACCCC
CCTAAATTTAGCTCTGCTGCAGGCCGCTGGCAAGGCATGTAGGGCAGGGCAGTCGTTTGC
CACGCGGTCCGGCTCGCTTAACACGTGGTTTGAATATATATTTTTACTCAGACACGCGA
TAGAAAAAAGATGCCGGAGTTAGGGAGAGAAAAAGAAAGGGGAATATTCCTTGTCCAGCG
AAGAGCTAGGCCACACCCACACGATATGGACTGCACTGCACGTACTGGGATATTCGGTAT
CCTGGTCACCCCGGCATTATTTGGACAATATATATATGTAGGGGCGGGTCCGCGATCCCA
AAGTCGGACGCGCTACGTGTTATTTGGACGCCTGGAACCTCTCTCGTTTCTCACGTGGGA
CTATCGTACCCCTACTCTACGTGTATCTATATCGTGCTCGTCACATGACACGCACACCAC
TTGTCGGTAGACAGACATCGGCCCCCAAGAACCGAAGTGCTACGCCCTCTCCCCGACCAC
TGCACACTGGTGCCTGTCGCACTGTATGAGAGATGCGTGGCTCGGCAAATTCGGAGCGGA
TTAATGTCGTCACCAAGAAACTAGAAACCACTTGCGTTCGTCACCTTTCATGGACCCCAG
CAGCTGCAGCAATCCTGCCAACGGAAACGCGCGCACATGGTGCATTAGTTCGCGTGGACG
CCGCTGCGATCCTTCATTTCGTTTCGTTTATTTACTATACTCGCGCGCGCCGCAGCTAGC
TATGGTTGTTAGATCACCAGCACGCGTATTGATTGCCACATGTGCCTGCCGCCTGGACTG
GACCTGCAGTGCAGCTCCTGTCCTGTGCACGCCTCTCCCTGCTGTTCTTAGTCTCATCAA
CCTCAAGTTTCATTCTTCTTTTCTTCTCCCCGCAGGTGGTCCCTGATCGCCGGTCACTTG
CCCGGTCGAACAGACAACGAGATCAAAAACTACTGGAACTCGCACCTGAGCAGCGGGCG
GCCGACTTCCGCGACGGCGTCGTCGTCGACATCGACCTCAGCAAGCTGCCCGGCGGCGGG
AAACGGCGCGGCGGCCGGGCCAGCCGGGGCGCCGTCGTGGCCGCGGCCAAGGAGAAGAAG
GCCAAGGAGAAGGACGACAGGGGCAATAGCAAGGTCGCAGAAGCGGAGCAGCAGCTCAGG
GACACGGAGGACGACGACGGCGGCAGCGTCTCCACGCCGAGGCCTCAGTCTGATGACTGC
GGCACCGCCCAGAGCGAAGAGGAGCAAGCGCAGGCCAGCGCCAGCGGCCTGACATCCGAT
GGGCATGGGCCCGAGGAGGAGGAGGAGGAGGACCCGCTGGCTCTGAGCGAGGAGATGGTG
```

Fig. 3B

```
AGTGCGCTTCTGGCCCCGGAAAGCCCAAAGCTGGAGGTGGGCCCCGATGGCTCGTGCATG
GACAGCTACAGTGGCCCTCCGTCAGGGGAAAGCGGCTGTGGGTCCAGTGGGCCTTCTGGC
GACGTGGCCCAGGACCTGGACCTAGACGACGACAAGGCCATCATGGACTGGGACTTGATG
GGGCTGGGACATCTCGACCCGCCGGTGACATGTGGGACCAGCTGGTGTGGGACTACGACG
AAACGTTGGTCACGGAACCGGAAGGAGGGGAGGAAGGGCACCAGCAGCAGGACGATGTCA
TGTCAGACCTCTTCTTCCTGGACAATCTCTAGGAGGTGCGAGGATAGCATGGGCATGGCT
GCCGTGATGCTTTATGCTTTTTAATTTGATCCGGTACTTGTAGGTTTTTGGGTGTGTTCA
GTTCAAAGATGAGTGGCGGTGTCAGAGACGAGATAAGGGGAGTGCTCCAGTGACATCTTT
GTTTGCTGGCCGGATCTCACGAACCCGTAGAATGGCAAGAATGTAGAAAAATAAGCACGC
AATATCACTTGGAAACCTTTCATCAGTAGAGCCTGTCTAACATCTACAGACGGAGAAATG
CAAAAAAAAAAAAAAAGGTTGCTGGGGTTATAAAAAAAAAAAAAAAAAAAAAAAAAAA
AAAAA
```

Fig. 4 sequence of ZmMYB-IF35

```
MGRAPCCEKVGLKKGRWTKEEDEVLARYIKEHGEGSWRSLPKNAGLLRCGKSCRLRWINY
LRAGLKRGNISEEEEDMIIKLHATLGNRWSLIAGHLPGRTDNEIKNYWNSHLSRRAADFR
DGVVVDIDLSKLPGGGKRRGGRASRGAVVAAAKEKKAKEKDDRGNSKVAEAEQQLRDTED
DDGGSVSTPRPQSDDCGTAQSEEEQAQASASGLTSDGHGPEEEEEEDPLALSEEMVSALL
APESPKLEVGPDGSCMDSYSGPPSGESGCGSSGPSGDVAQDLDLDDDKAIMDWDLMGLGH
LDPPVTCGTSWCGTTTKRWSRNRKEGRKGTSSRTMSCQTSSSWTISRRCEDSMGMAAVML
YAF
```

(a) IF35 transgenic lines grown on a 3% sucrose medium without nitrogen. All lines show the accumulation anthocyanin pigments near and around the cotyledons. (b) Pigmented and non pigmented seed coat colorations due to accumulation of tannins showed by IF35 transgenic line 10 in the second generation and line 2 in the third generation.

TRANSGENIC PLANTS WITH ALTERED LEVELS OF PHENOLIC COMPOUNDS

This application is a divisional application of U.S. patent application Ser. No. 10/093,837, filed Mar. 8, 2002, which is now U.S. Pat. No. 7,154,023, which claims priority to U.S. Provisional Application No. 60/274,629, filed Mar. 8, 2001, the entirety of which are incorporated by reference herein.

The present invention was made, at least in part, with support from the Department of Agriculture (Grant No. USDA 1999-01582)) and the National Science Foundation (Grant No. MCB-9974474 and MCB-9896111). The United States Government has certain rights in the invention.

BACKGROUND

Definitions

Antisense—As used herein refers to a single-stranded nucleic acid, typically RNA, having a complementary base sequence to the base sequence of a messenger RNA (mRNA).

Complementary—As used herein refers to a nucleotide sequence that is related to another nucleotide sequence by the Watson-Crick base-pairing rules, i.e., the sequence A-T-G-C in a DNA strand is complementary to the sequence T-A-C-G in a second DNA strand and to the sequence U-A-C-G in an RNA strand.

Double-stranded RNA (dsRNA)—As used herein refers to polyribonucleotide structure formed by either a single self-complementary RNA strand or by at least two complementary RNA strands. The degree of complementary need not necessarily be 100 percent. Rather, it must be sufficient to allow the formation of a double-stranded structure under the conditions employed.

Gene expression or expression—As used herein refers to the presence of an RNA transcribed from a gene or a protein translated from an RNA transcribed from the gene within a call, tissue, or organism. More specifically, gene expression can be evaluated with respect to RNA expression or protein expression. The term "gene expression" is also used to refer to the process by which RNA is transcribed from a gene or by which RNA transcribed from a gene is translated.

Sense—As used herein, refers to a base sequence as present in a messenger RNA (mRNA).

Vector—As used herein, refers to a nucleic acid molecule capable of mediating introduction of another nucleic acid to which it has been linked into a cell. One type of preferred vector is an episome, i.e., a nucleic acid capable of extra-chromosomal replication. Preferred vectors are those capable of extra-chromosomal replication and/or expression of nucleic acids to which they are linked in a host cell. Vectors capable of directing the expression of inserted DNA sequences are referred to herein as "expression vectors" and may include plasmids or viruses, in particular baculoviruses. However, the invention is intended to include such other forms of expression vector which serve equivalent functions and which become known in the art subsequently hereto.

Plants provide an almost endless variety of chemical compounds derived from primary or secondary metabolism. Many plant secondary metabolites are desirable. For example, some plant secondary metabolites provide protection against pathogens or adverse environmental conditions, and thus have substantial agronomic importance. In addition, a number of plant secondary metabolites serve as nutraceutical components of our diet. Furthermore, certain plant secondary metabolites have diverse medical applications, particularly in the pharmaceutical industry (See, Heilmann J. and R. Bauer (1999) *Functions of Plant Secondary Metabolites and their Exploitation in Biotechnology*. M. Wink. Boca Raton, CRC Press LLC. 3: 274-310).

The accumulation of certain secondary metabolites in plants, however, can also be problematic. For example, the presence in trees of large amounts of lignin, a product of the plant phenylpropanoid pathway, can increase the costs and time required to make high quality paper. Large amounts of lignin in grasses can decrease their digestibility. In flour products, high levels of colored pigments, which are also products of the phenylpropanoid pathway, can make the flour products less desirable to the consumer.

Plant secondary metabolites can be grouped into several major classes including the phenolics, alkaloids, and isoprenoids. The amino acids phenylalanine and tyrosine serve as precursors for phenolic compounds that are intermediates or final products of a branch of the phenylpropanoid pathway. A schematic representation of the plenylpropanoid pathway which leads from phenylalanine through several branches to the hydroxy cinnamates, lignins, and the flavonoids is shown in FIG. 1. The phenylpropanoids, and their derivatives, and the flavonoids, and their derivatives, are examples of intermediates and final products of the phenylpropanoid pathway respectively. Flavonoids are phenolic natural products that have multiple functions in plants, including roles as floral pigments for the attraction of pollinators, signaling molecules for beneficial microorganisms in the rhizosphere, and antimicrobial defense compounds. In addition, flavonoids are emerging as important nutraceuticals because of their strong antioxidant properties, and several flavonoids show anti-tumor activities. Chlorogenic acid, another phenolic compound that is believed to be the final product of one branch of the phenylpropanoid pathway has anti-pathogenic activity and bactericidal activity in plant and anti-tumor activity in animals.

The first committed step in the phenylpropanoid pathway is catalyzed by phenylalanine ammonia lyase (PAL), which converts phenylalanine to cinnamic acid (or tyrosine to ρ-coumaric acid in some monocots). Transcriptional activation of genes encoding enzymes involved in phenylpropanoid metabolism, such as PAL, 4-coumarate CoA ligase (4CL), and cinnamyl alcohol dehydrogenase (CAD), represents a key step in the regulation of the phenylpropanoid pathway. The coordinate regulation of the PAL, 4CL and CAD genes in many plant species suggests the existence of specific transcription factors or transactivators that coordinately activate the expression of these genes.

The regulation of flavonoid biosynthesis provides the best described example of how certain transcription factors control the expression of biosynthetic genes (reviewed in Mol et al. 41). In maize, two classes of regulatory proteins control accumulation of the anthocyanins which are flavonoid derivatives. These two classes are a Myb-domain containing class (encoded by the CI and P1 genes) and a basic helix-loop-helix (bHLH)-domain containing class (members of the RIB gene families). Anthocyanin production requires the interaction between a member of the Myb-domain C1/P1 family and a member of the bHLH-domain R/B family 41, and the pattern of anthocyanin pigmentation in any particular plant part is controlled by the combinatorial, tissue-specific expression of these regulatory genes. Orthologs, as defined by Fitch, of the maize C1 and R regulators have been identified in other plants, such as petunia and snapdragon, and these regulatory proteins have been shown to be exchangeable between monocots and dicots.

In addition to 3-hydroxy flavonoids and anthocyanins, maize and its close relatives like sorghum accumulate 3-deoxy flavonoids and derived pigments, which include the phlobaphenes. A single known transcription factor (P) controls 3-deoxy flavonoid and phlobaphene biosynthesis in maize. P regulates the accumulation of a subset of flavonoid biosynthetic gene products, namely C2 (a chalcone synthase) and A1 (dihydroflavonol 4-reductase). On the basis of these and other studies, it is quite clear that transcription factors are important tools for controlling the levels of flavonoids in plants.

In view of the important role of phenolic compounds that are intermediates and final products of the plant phenylpropanoid pathway, it is desirable to have additional transcription factors which are capable of regulating the levels of these secondary metabolites in plants. Such transactivators would serve as important tools for increasing pathogen resistance, altering digestibility, and manipulating levels of nutraceutical compounds, such as flavonoids and other phenolic compounds, in plants.

SUMMARY OF THE INVENTION

The present invention provides methods for altering levels in plants of one or more phenolic compounds that are intermediates or final products of the plant phenylpropanoid pathway. One method comprises transforming a plant cell with an expression construct, hereinafter referred to as the "ZmMyb-IF35 sense construct" comprising a DNA molecule or transgene comprising a sequence which encodes a transactivator protein comprising the myb domain of a protein referred to hereinafter as the maize "ZmMyb-IF35" protein or a functional equivalent thereof and an activation domain; and regenerating a transgenic plant from the transformed plant cell. The transgene further comprises a promoter operably linked to the transactivator protein encoding sequence. In one embodiment, the transactivator protein comprises the activation domain as well as the myb domain of the maize ZmMYB-IF35 protein. Another method comprises transforming a plant cell with an expression construct, hereinafter referred to as the "ZmMyb-IF35 antisense construct" comprising a DNA molecule or transgene comprising a sequence which encodes an antisense ZmMyb-IF35 RNA and a promoter operably linked to the antisense ZmMyb-IF35 RNA coding sequence; and regenerating a transgenic plant from the transformed plant cell. The antisense ZmMyb-IF35 RNA has a sequence with sufficient complementarity to the wild-type maize ZmMyb-IF35 protein encoding sequence to prevent its translation or to ensure the degradation of the sense ZmMyb-IF35 RNA in the cell. Another method comprises transforming a plant cell with an expression construct, hereinafter referred to as the "ZmMyb-IF35 dsRNAi construct" comprising a DNA molecule or transgene comprising a sequence which encodes a ZmMyb-IF35 sense RNA coding sequence and a ZmMyb-IF35 antisense RNA coding sequence, a linker sequence which links the ZmMyb-IF35 sense RNA coding sequence to the ZmMyb-IF35 antisense RNA coding sequence, and a promoter operably linked to the ZmMyb-IF35 sense RNA coding sequence and the ZmMyb-IF35 antisense RNA coding sequence; and regenerating a transgenic plant from the transformed plant cell.

The present invention also relates to a method of altering levels in a plant of one or more phenolic compounds that are intermediates or a final product of the phenylpropanoid pathway by introducing into such cells an RNA molecule comprising a sequence which encodes a transactivator protein comprising the myb domain of the maize ZmMyb-IF35 protein or a functional equivalent thereof and an activation domain; and expressing the transactivator protein in the cell.

The present invention also relates to the ZmMyb-IF35 sense, antisense, and dsRNAi expression constructs and vectors which are used in the present methods. The present invention also relates to transformed plant cells and transgenic plants prepared according to the present methods, and the seeds of such transgenic plants. Such transgenic plants comprise altered levels of one or more phenolic compounds that are intermediates of final products of the phenylpropanoid pathway.

BRIEF DESCRIPTION OF THE FIGURES

FIG. 3 shows the nucleotide sequence, SEQ ID NO. 1, of a genomic DNA molecule which encodes the maize ZmMyb-IF35 protein. The sequence comprises the nucleotide sequences of a portion of the 5' untranslated region, exon 1, intron 1, exon 2, intron 2, and exon 3 of the maize ZmMyb-IF 35 gene.

FIG. 4 shows the deduced amino acid sequence, SEQ ID NO. 2 of the maize ZmMyb-IF 35 protein.

FIG. 7(*b*) shows the absence of pigments in seeds derived from transgenic *Arabidopsis* plants which comprise a transgene comprising a sequence which encodes the ZmMyb-IF35 protein operably linked to a CaMV 35S promoter.

DETAILED DESCRIPTION OF THE INVENTION

Figure 1A:
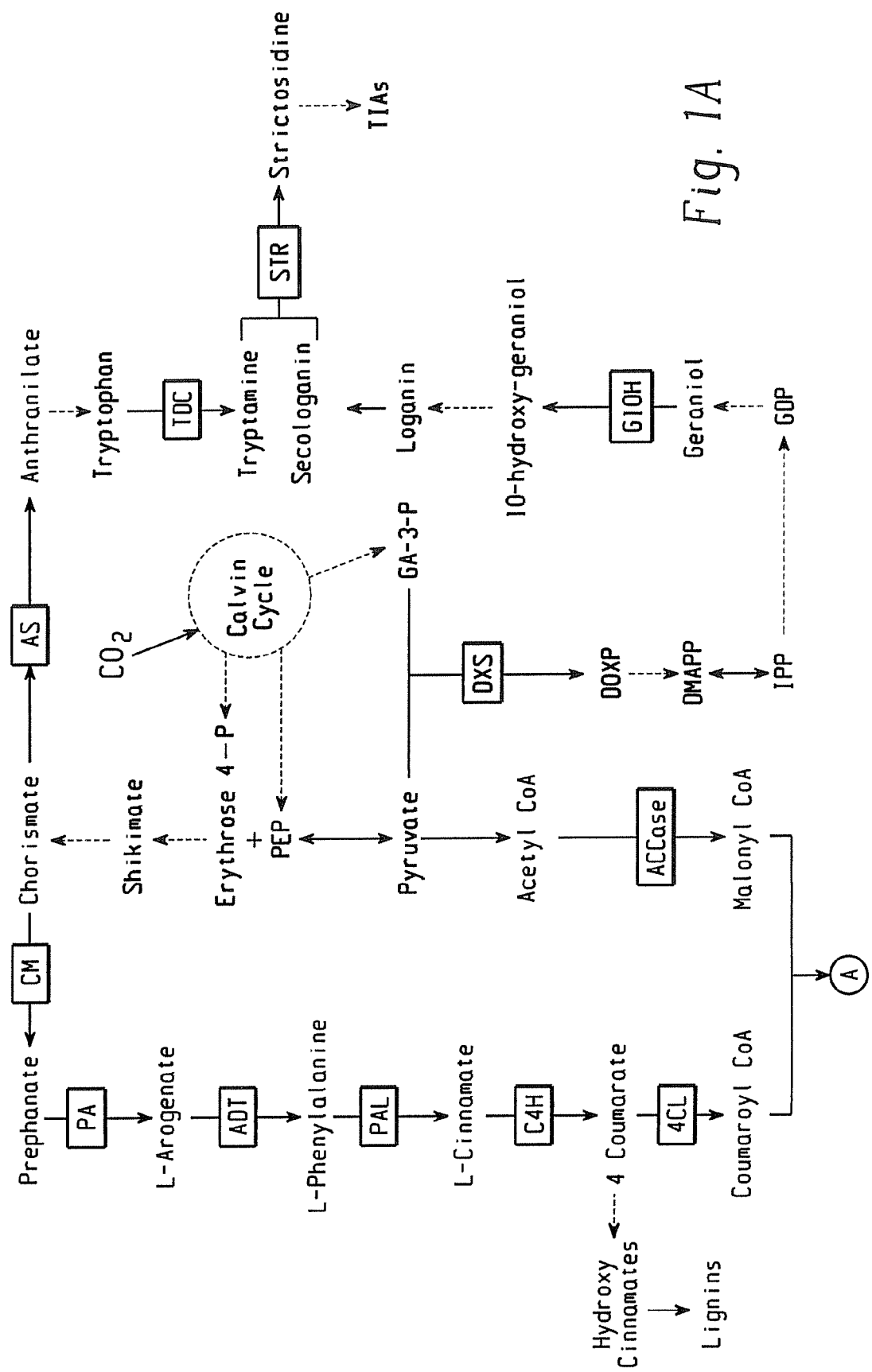
FIG. 1 is a schematic representation of the phenylpropanoid and terpenoid indole alkaloid biosynthetic pathways. Only the core enzymes of each pathway are shown, and the names of classes of intermediates or final compounds are indicated. Compounds and enzymes from primary metabolism are shown in regular type. Compounds and enzymes involved in the secondary metabolic pathway are shown in bold type.
Figure 1B:
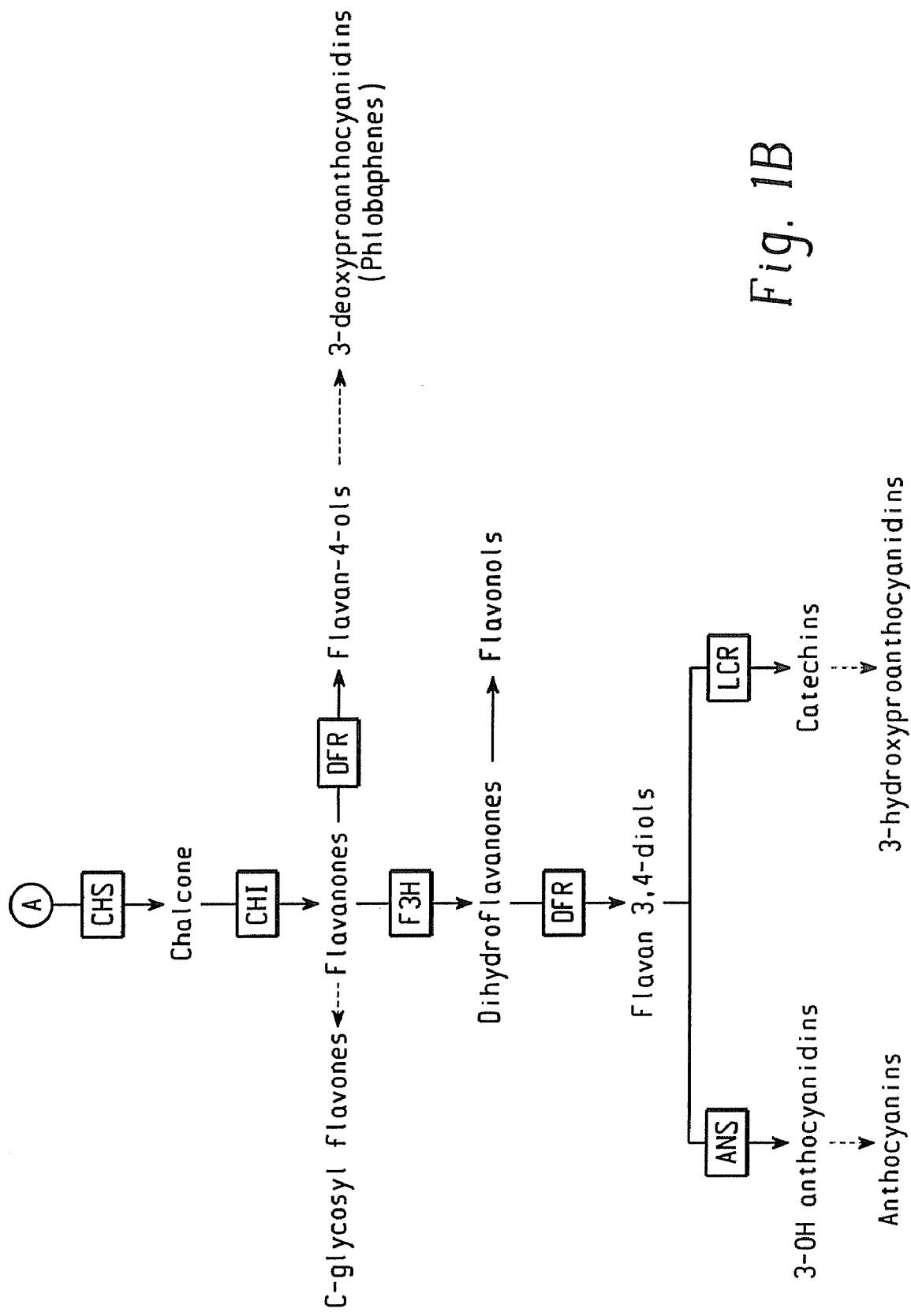
Figure 2:
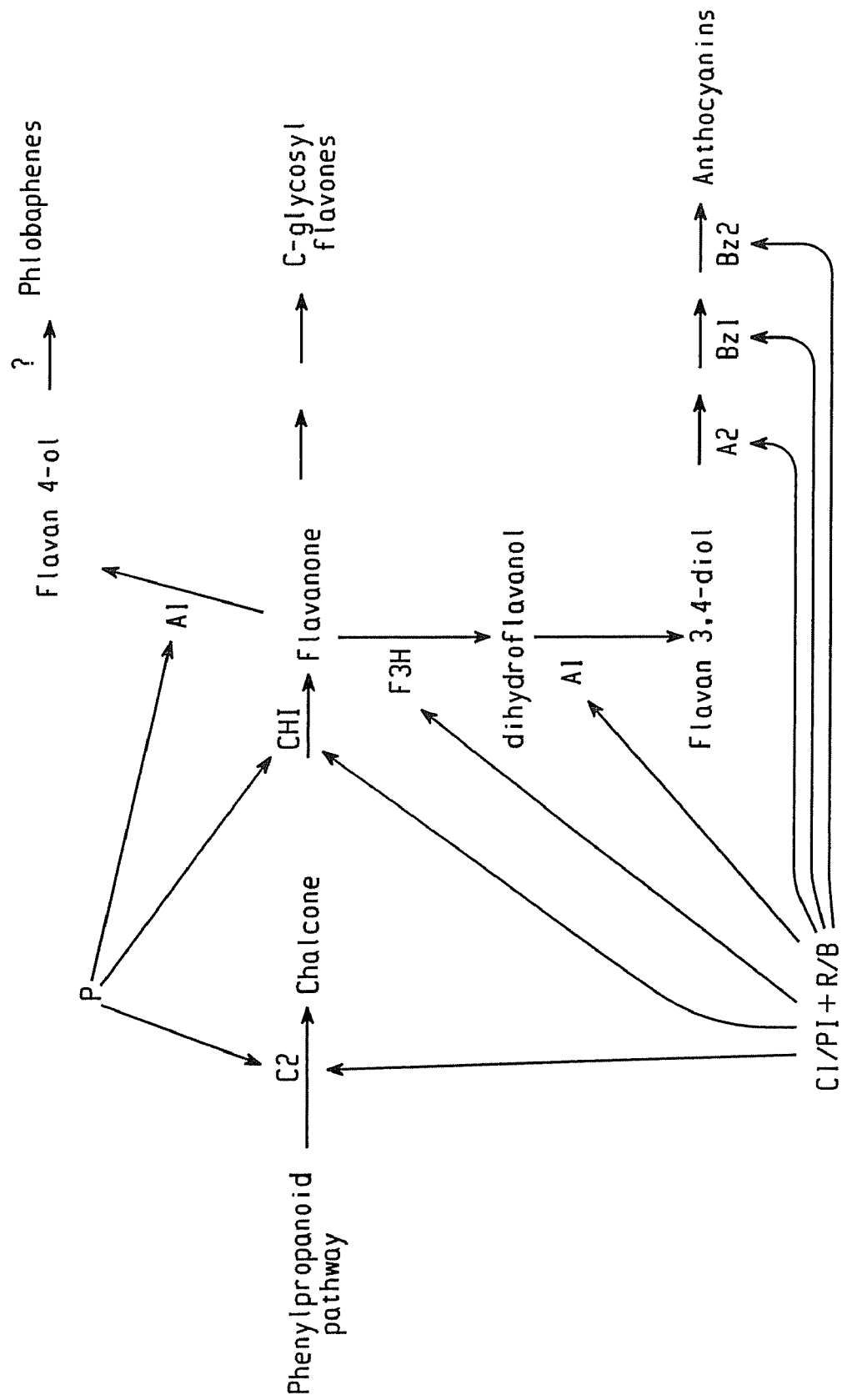
FIG. 2 is a schematic representation of the regulation of the maize anthocyanin biosynthetic pathways by the transcription factors P and C1/PI+R/B.
Figure 5:
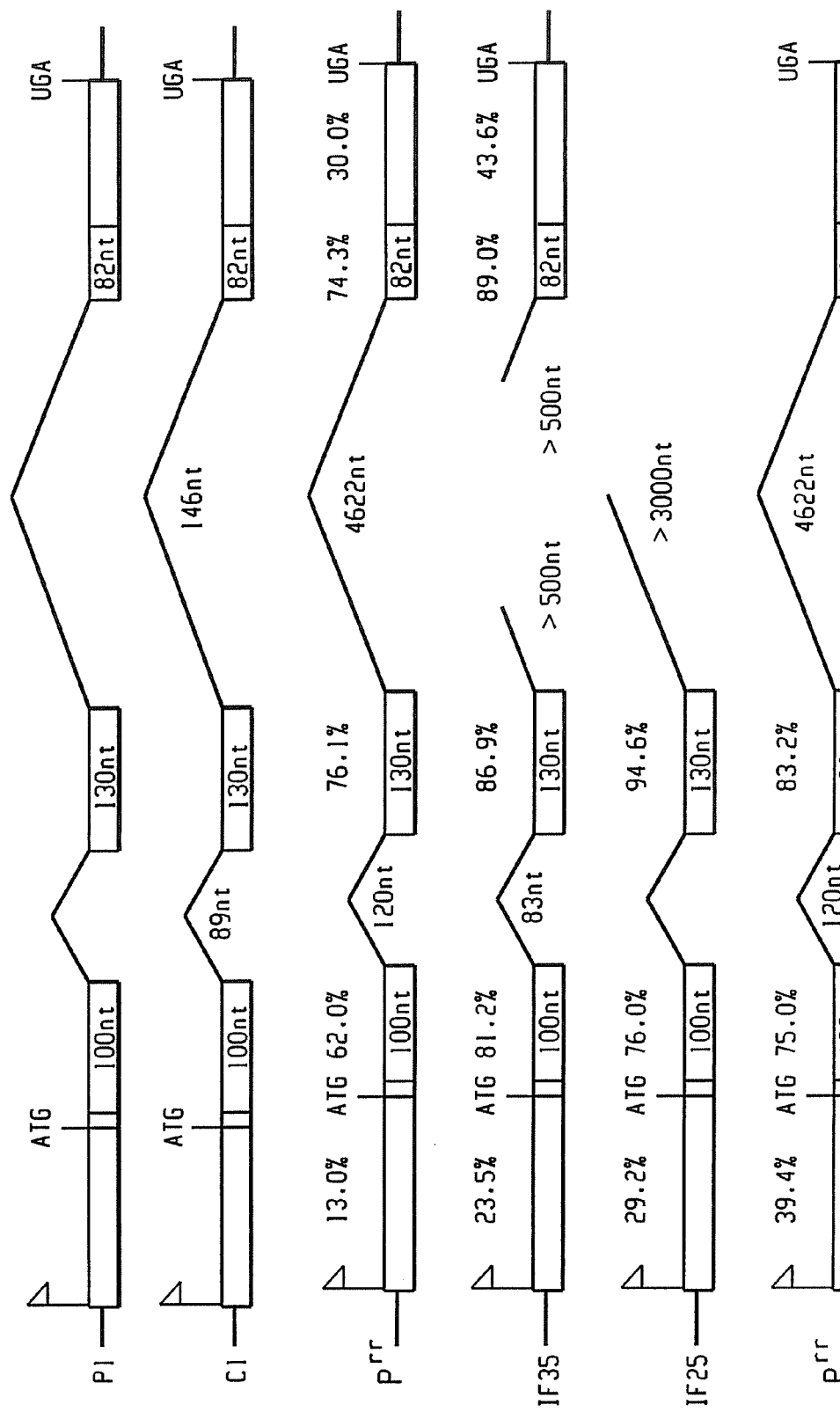
FIG. 5 is an alignment of an allele (Prr) which encode the maize transcription factor P and the maize ZmMyb-IF35 gene.

The present invention provides sense, antisense, and dsRNAi expression constructs which can be used to prepare transgenic plant cells, plant parts, and plants having elevated or depressed levels of one or more phenolic compounds that are intermediates or final products of the phenylpropanoid pathway. One example of a phenolic compound that is believed to be the final product of one branch of the phenylpropanoid pathway is chlorogenic acid. It is also believed that coumaryl coA (See FIG. 1) is a precursor required for chlorogenic acid formation. Chlorogenic acid has anti-fungal activity and bactericidal activity in plants and anti-tumor activity in animals. An example of a phenolic compound that is believed to be an intermediate in the lignin branch of the phenylpropanoid pathway is ferulic acid.

The ZmMyb-IF35 sense construct comprises a DNA molecule comprising a sequence that encodes a transactivator protein comprising the myb domain of the maize ZmMyb-IF35 protein, or a functional equivalent thereof, and a transactivation domain. The sense construct further comprises a promoter operably linked to the transactivator protein encoding sequence. Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are covalently linked contiguous. However, enhancers do not have to be contiguous. Linking is accomplished by ligation at convenient restriction sites. If such sites do not exist, synthetic oligonucleotide adapters or linkers are used in accordance with conventional practice.

Another sense construct useful for altering the levels in plant cells of phenolic compounds that are intermediates or final products in the phenylpropanoid pathway comprises an RNA molecule comprising a sequence which encodes a transactivator protein comprising the myb domain of the maize ZmMyb-IF35 protein, or a functional equivalent thereof, and a transactivation domain. Such RNA molecule is operably linked to regulatory sequences which permit translation of the RNA molecule within plant host cells.

The ZmMyb-IF35 antisense construct comprises a DNA molecule comprising a sequence which encodes an antisense RNA molecule comprising a sequence with sufficient complementarity to the maize ZmMyb-IF35 RNA coding sequence to stably bind thereto, and thus, prevent its translation. The antisense RNA comprises at least 15 nucleotides. The ZmMyb-IF35 antisense construct further comprises a promoter operably linked to the antisense RNA encoding sequence.

The ZmMyb-IF35 dsRNAi construct comprises a DNA molecule or transgence comprising a sequence which encodes a sense ZmMyb-IF35 RNA coding sequence and an antisense ZmMyb-IF35 RNA coding sequence and a linker sequence which links the sense ZmMyb-IF35 RNA coding sequence to the antisense ZmMyb-IF35 RNA coding sequence. The linker is at least 300 in length, and preferably, from 400 to 500 base pairs in length. One example of such a linker is a 400 bp from ff in the bacterial UdA encoding GUS. The transgene is operably linked to a promoter which drives expression of the sense ZmMyb-IF35 RNA and the antisense ZmMyb-IF35 RNA. The double-stranded RNA that results from expression of this construct prevents accumulation of ZmzMyb-IF35 mRNA through a post-transcription gene silencing method known in the art as double-stranded RNA interference.

ZmMyb-IF35

As used herein the term "ZmMyb-IF35" refers to a maize Myb protein which has a molecular weight of about 38 kDa and comprises an N terminal R2R3 myb domain. In one embodiment, the maize ZmMyb-IF35 protein has the amino acid sequence, SEQ ID NO. 2, shown in FIG. 4. The nucleotide sequence, SEQ ID NO. 1, of a genomic DNA molecule which encodes this form of the maize ZmMyb-IF35 protein is shown in FIG. 3. The 5' untranslated region (5'UTR) of this DNA molecule extends from nucleotide 1 through 197 of SEQ ID NO. 1. The first exon sequence extends from nucleotide 198 through 321; the second exon sequence extends from nucleotide 415 through 544, and the third sequence extends from nucleotide 2736 through nucleotide 3564. The nucleotide sequence encoding the myb domain of maize ZmMyb-IF35 begins at nucleotide 232 within exon 1, encompasses all of exon 2, and ends at nucleotide 2817 within exon 3.

The amino acid sequence of the Myb domain of maize ZmMyb-IF35, which extends from amino acid 12 through amino acid 115 in SEQ ID NO. 2, has 86% identity to the amino acid sequence of the Myb domain of the maize P protein. Outside of the Myb domain, the amino acid sequence of ZmMyb-IF35 has only 33% identity with the amino acid sequence of the maize P protein. The % of amino acid identity was determined using Cluatal-W formatted Alignments.

Transactivator Protein

The transgene encoding the transactivator protein comprises a sequence which encodes the maize ZmMyb-IF35 myb domain or a functional equivalent thereof and a sequence which encodes an activation domain. The term "functional equivalent" as used herein refers to a polypeptide whose amino acid sequence is at least 95% identical, preferably 97% identical, more preferably at least 99%, identical to the amino acid sequence which includes and extends from amino acid 12 through amino acid 115 of SEQ ID NO. 2. Such functional equivalents when linked to an activation domain and incorporated into a maize cell enhance production of chlorogenic acid in the resulting transformed maize host cells in the same manner and to the same extent as the naturally-occurring maize ZmMyb-IF35 protein. Levels of chlorogenic acid in the transformed host cells are assayed using standard techniques such as high performance liquid chromatography (HPLC).

Such functional variants have an altered sequence in which one or more of the amino acids is deleted or substituted, or one or more amino acids are inserted, as compared to the reference amino acid sequence, i.e., amino acid 12 through amino acid 115 of SEQ. ID. NO.:2. Sequences which are at least 95% identical have no more than 5 alterations, i.e. any combination of deletions, insertions or substitutions, per 100 amino acids of the reference amino acid sequence. Percent identity may be determined by comparing the amino acid sequence of the functional variant with the reference sequence, i.e. the sequence extending from and including amino acid 12 through amino acid 112 in SEQ ID NO. 2 using MEGALIGN project in the DNA STAR program. The variant sequences and reference sequences are aligned for identity calculations using the method of the software basic local alignment search tool in the BLAST network service (the National Center for Biotechnology Information, Bethesda, Md.) which employs the method of Altschul, S. F., Madden, T. L., Shäffer, A. A., Zhang, J., Zhang, Z., and Miller, W. (1997) Nucleic Acid Res. 25, 3389-3402. Identities are calculated, for example, by the Align program (DNAstar, Inc.) In all cases, internal gaps and amino acid insertions in the candidate sequence as aligned are not ignored when making the identity calculation. Preferably, the substitutions, deletions, or additions are made at the positions marked with an X in the maize ZmMyb-IF35 myb domain sequence, SEQ ID NO. 2, shown below.

Myb Domain Amino Acid Sequence of IF35

LKXGRWTXEEDXXLAXYIXEHGEGSWRSLPKNAGLLRCGKSCRLRWINYL

RAXXKRGNIXXEEEDXIXKLHATLGNRWSLIAXHLPGRTDNEIKNYWNSH

LSRX

While functional variants of the myb domain of the maize ZmMyb-IF35 protein may have non-conservative amino acid substitutions, it is preferred that the functional variant have the conservative amino acid substitutions. In conservative amino acid substitutions, the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The term "activation domain" as used herein refers to a peptide which allows the transactivator protein to interact with an RNA polymerase or with components of the basal transcription machinery. The activation domain may be directly linked by a peptide bond to the C terminus of the ZmMyb-IF35 myb domain or its functional equivalent. Alternatively, there may be a linker comprising from 1 to 500 amino acids between the C terminus of the ZmMyb-IF35 myb domain or its functional equivalent and the N terminus of the activation domain. The activation domain may have a sequence which is at least 95% identical, preferably 97% identical, more preferably at least 99%, identical to the amino acid sequence which includes and extends from amino acid 116 through amino acid 345 of SEQ ID NO. 2. Alternatively the activation domain may be derived from another myb protein. Examples of other sources for the activation domain include, but are not limited to, the maize C1 regulator protein, the yeast Gal4 protein, and the VP16 protein from herpes virus.

Examples of nucleotide sequences which encode the transactivator proteins of the present invention include, but are not limited to, a sequence which encodes amino acid 1 through amino acid 345 of SEQ ID NO. 2, a sequence which comprises the sequences of the first, second and third exons of SEQ ID NO. 1, and a sequence which binds under highly stringent hybridization conditions to a sequence which comprises nucleotide 232 through nucleotide 331, nucleotide 415 through nucleotide 544, and nucleotide 2736 through nucleotide 3564 of SEQ ID NO. 1. Hybridization conditions are based on the melting temperature TM of the nucleic acid binding complex or probe, as described in Berger and Kimmel (1987) Guide to Molecular Cloning Techniques, Methods in Enzymology, Vol. 152, Academic Press. The term "stringent conditions", as used herein, is the "stringency" which occurs within a range from about Tm-5 (5° below the melting temperature of the probe) to about 20° C. below Tm. "Highly Stringent hybridization conditions" refers to an overnight incubation at 42 degree C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.2×SSC at about 65 degree C. for 30 minutes. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Construct

The ZmMyb-IF35 sense, antisense, and dsRNAi expression constructs further comprise a promoter which is operably linked to the transactivator protein encoding sequence or the ZmMyb-IF35 antisense RNA encoding sequence, or the ZmMyb-IF-35 antisense RNA and sense RNA coding sequences, respectively. The promoter may be constitutive, inducible or tissue specific promoter.

The promoters may be obtained from genomic DNA by using polymerase chain reaction (PCR), and then cloned into the construct. Standard recombinant DNA and molecular cloning techniques used here are well known in the art and are described by J. Sambrook, E. F. Fritsch and T. Maniatis, Molecular Cloning: A Laboratory Manual, Cold Spring Harbor Laboratory, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984).

Optionally, the ZmMyb-IF35 sense and antisense constructs further comprise a transcriptional terminator which is operably linked to the transactivator protein encoding sequence or the ZmMyb-IF 35 antisense RNA sequence, respectively. A variety of transcriptional terminators are available for use in the expression constructs. These are responsible for the termination of transcription beyond the transgene and its correct polyadenylation. Appropriate transcriptional terminators and those which are known to function in plants include the CaMV 35S terminator, the tml terminator, the nopaline synthase terminator and the pea rbcS E9 terminator.

Optionally, the construct further comprises sequences for the enhancement or regulation of expression. Numerous sequences have been found to enhance gene expression from within the transcriptional unit and these sequences can be used in conjunction with the DNA molecules of this invention to increase their expression in transgenic plants. Various intron sequences have been shown to enhance expression, particularly in monocotyledonous plants. For example, the introns of the maize Adh1 gene have been found to significantly enhance the expression of the wild-type gene under control of its cognate promoter when introduced into maize cells. Intron 1 was found to be particularly effective and enhanced expression in fusion constructs with the chloramphenicol acetyltransferase gene (Callis et. al., Genes Develop. 1:1183-1200, 1987). In the same experimental system, the intron from the maize bronze 1 gene had a similar effect in enhancing expression (Callis et al., supra). Intron sequences have been routinely incorporated into plant transformation vectors, typically within the non-translated leader.

A number of non-translated leader sequences, derived from viruses, are also known to enhance expression. Specifically, leader sequences from Tobacco Mosaic Virus (TMV, the "omega sequence"), Maize Chlorotic Mottle Virus (MCMV), and Alfalfa Mosaic Virus (AlMV) have been shown to be effective in enhancing expression (e.g., Gallie et. al., Nucl. Acids Res. 15:8693-8711, 1987; Skuzeski et. al., Plant Mol. Biol. 15:65-79, 1990).

The constructs of the present invention are synthesized by insertion of a sequence comprising the transactivator protein encoding sequence or the antisense RNA encoding sequence or both into an empty expression cassette. Such empty expression cassettes, providing appropriate regulatory sequences for plant expression of the encoding sequence are well-known. To produce the transactivator protein, the protein encoding sequence is placed in correct orientation in the construct. The transgene preferably employs plant-preferred codons to enhance expression of the transgene. To produce an antisense mRNA which can interfere with indigenous production of the ZmMyb-IF35 protein, the ZmMyb-IF35 protein encoding sequence is placed in the expression construct in the opposite orientation. The nucleotide sequence of the transgene, either DNA or RNA, can readily be derived from the amino acid sequence for the protein using standard texts. The transgene preferably employs plant-preferred codons to enhance expression of the transgene.

The present invention also provides a vector, such as for example a plasmid, which comprises the expression construct The term "vector" as used herein refers to DNA molecules which are able to replicate and to express a foreign gene in a host cell. Typically, the vector has one or more restriction endonuclease recognition sites which permit insertion of the expression construct or transgene into the vector. Preferably, the vector further comprises a marker gene, such as for example, a dominant herbicide resistance gene or antibiotic resistance gene, which encode compounds that serve to identify and separate transformed cells from non-transformed cells. Examples of suitable marker genes include the bar gene which codes for phosphinothricin acetyl transferase, a kanamycin resistance gene, and a hygromycin resistance gene. A cell in which the foreign genetic material in the vector is functionally expressed has been "transformed" by the vector and is referred to as a "transformant". Expression of the transactivator protein encoding sequence and the antisense RNA encoding sequence in transformants may be monitored using Northern blot techniques.

Optionally, the vector may include partial T-DNA border sequences, typically retained on integrated DNA following a T-DNA insertion event. Alternately, the integrated exogenous DNA may show some truncation of the left end of the T-DNA, or occasionally, of some DNA beyond the left border, as has been observed after transformation with *Agrobacterium*.

Vectors suitable for transforming plant cells include, but are not limited to, Ti plasmids from *Agrobacterium tumefaciens* (J. Darnell, H. F. Lodish and D. Baltimore, Molecular Cell Biology, 2nd edition, Scientific American Books, N.Y. (1990)), a plasmid containing a β-glucuronidase gene and a cauliflower mosaic virus (CaMV) promoter plus a leader sequence from alfalfa mosaic virus (Sanford et. al., Plant Mol. Biol. 22:751-765, 1993) or a plasmid containing a bar gene cloned downstream from a CaMV 35S promoter and a tobacco mosaic virus (TMV) leader. Other plasmids may additionally contain introns, such as that derived from alcohol (Adh 1), or other DNA sequences. The size of the vector is not a limiting factor.

Transformation of Plant Cells

Any type or source of plant cells which can serve as a target for transformation by any one or more of the various biological and non-biological delivery mechanisms available in the art can serve as a target for transformation according to the present method. These include, but are not necessarily limited to, immature and mature embryos, pollen, protoplasts, suspension culture cells, callus cells, cotyledons or other seed and seedling parts, leaves or leaf pieces, and roots or root pieces.

Host cells which serve as the target from transformation can be derived from monocotyledonous or dicotyledonous plants. In preferred embodiments, the host cells are obtained from maize, rice, sorghum, cotton and soybeans.

The transformed host cells are useful for preparing transgenic plants or transgenic callus lines or cell lines with altered levels of phenolic compounds. The transformed host cells are also useful sources of important phenolic compounds. These compounds are extracted from the host cells using procedures known in the art.

Methods of Transforming Plant Cells

Delivery or introduction of the ZmMyb-IF35 sense and antisense expression contructs into the host plant cells, may be accomplished by a variety of techniques available in the art. Such techniques include non-biological mechanisms such as microprojectile bombardment, electroporation, microinjection, induced uptake, and aerosol beam injection, as well as biological methods such as direct DNA uptake, liposomes and *Agrobacterium*-mediated transformation. See, for example, Bilang, et. al., Gene 100:247-250, 1991; Scheid et. al., Mol. Gen. Genet. 228:104-112, 1991; Guerche et. al., Plant Science 52:111-116, 1987; Neuhause et. al., Theor. Appl Genet. 75:30-36, 1987; Klein et. al., Nature 327:70-73 1987; Howell et. al., Science 208:1265, 1980; Horsch et. al., Science 227:1229-1231, 1985; DeBlock et. al., Plant Physiology 91:694-701, 1989; Methods for Plant Molecular Biology, Weissbach and Weissbach, eds., Academic Press, Inc., 1988; and Methods in Plant Molecular Biology, Schuler and Zielinski, eds., Academic Press, Inc., 1989. See also, U.S. Pat. Nos. 4,945,050; 5,036,006; and 5,100,792, all to Sanford et. al. Combinations of the above methods may also be used.

Transformation of host cells derived from monocotyledonous plants, preferably, is achieved using microprojectile bombardment. As used herein "microprojectile bombardment" is used to refer to the general method of delivering nucleic acids, including DNA and RNA, to a living cell by coating or precipitating the nucleic acids onto a microprojectile, preferably gold particles, and propelling the coated microprojectile into the living cell (see e.g., U.S. Pat. No. 5,036,006 issued Jul. 30, 1991 to Sanford et. al.; U.S. Pat. No. 5,302,523, issued Apr. 12, 1994 to Coffee; Vasil et. al., Biotechnology 11:1553-1558, 1993; and Weeks et. al., Plant Physiol. 102:1077-1084, 1993).

The exact amount of the construct provided to the host cell is not critical and may vary depending on the manner and form in which the component is delivered. If desired, the skilled artisan may routinely vary the amount of construct delivered to determine the optimum level for each using a particular delivery system.

The successful delivery of the DNA or RNA construct into the host cell may be preliminarily evaluated by the transient expression of a "reporter" gene. A reporter gene is a component on the expression vector introduced into the cell, or a component of a separate DNA construct which is co-introduced into the cell along with the DNA construct comprising the transgene. The property conferred on the transformed cell or tissue by the introduction of the reporter gene is usually easily detectable (e.g., expression of an easily assayable enzyme). "Transient expression" denotes the expression of a gene before the gene has been stably integrated into the genome of the treated cells or tissue. For example, commonly used reporter genes are the genes coding for the production of chloramphenicol acetyltransferase, which confers resistance to the antibiotic chloramphenicol, or the E. coli β-glucuronidase gene (gusA), the products of which can be detected by a histochemical assay.

Cells that express reporter genes in transient assays may not give rise to cells where the transformed DNA becomes stably integrated into the host cell genome. Selection of cells that express various marker genes, however, does give rise to cells in which the transformed DNA is stably integrated into the host cell genome. Herein, "selection" means conditions where only cells into which the DNA construct has been delivered will grow and cells in which the DNA construct has not been delivered will not grow. For example, cells stably expressing an introduced neomycin phosphotransferase gene are selected by growth in the drug G418. Cells stably expressing an introduced herbicide resistance gene are selected by growth in the presence of the herbicide. Shoots or plantlets growing in the presence of the drug or herbicide are presumptively transformed. Confirmation of stable integration of the transformed genes into the genome of the host may later be accomplished by, for example, herbicide treatment of the resulting plants. In addition, later molecular detection of the introduced DNA in the isolated genomic DNA of the plant cells, for example using Southern blotting/hybridization or polymerase chain reaction, may be used to confirm integration of the introduced genes into the genome of the host.

Transformed plant host cells are used to regenerate transgenic plants. In plants, every cell is capable of regenerating into a mature plant and, in addition, contributing to the germ line such that subsequent generations of the plant will contain the transgene. Growth of transformed plant cells and regeneration of such cells into mature plants is routine among those skilled in the art.

The transgenic plants are then grown and pollinated with either the same transformed strain or with different strains, and the resulting hybrid, having the desired phenotypic characteristic, is identified. Two or more generations may be grown to ensure that the desired phenotypic characteristic is stably maintained and inherited and then seeds harvested. Transformed progeny obtained by this method may be distinguished from non-transformed progeny by the presence of the introduced transgene(s) and/or accompanying DNA in the genome of the plant. Transformed plants also may be distinguished from non-transformed plants by a change in phenotype. For example, transformed plants may be distinguished from non-transformed plants by the presence of the transactivator protein or antisense RNA in tissues or cells where it is not normally not present or by an increase or decrease in the amount of the transactivator protein in cells where it normally is present.

The present invention also encompasses plant cells which are transiently transfected with an RNA molecule which encodes a transactivator protein comprising a ZmMyb-IF35 myb domain and an activation domain. Such cells are useful for producing large amounts of desirable phenolic compounds that are intermediates or final products of the phenylpropanoid pathway.

EXAMPLES

The following examples are for purposes of illustration only and are not intended to limit the scope of the invention as defined in the claims which are appended hereto. The references cited in this document are specifically incorporated herein by reference.

Example 1

Figure 6:
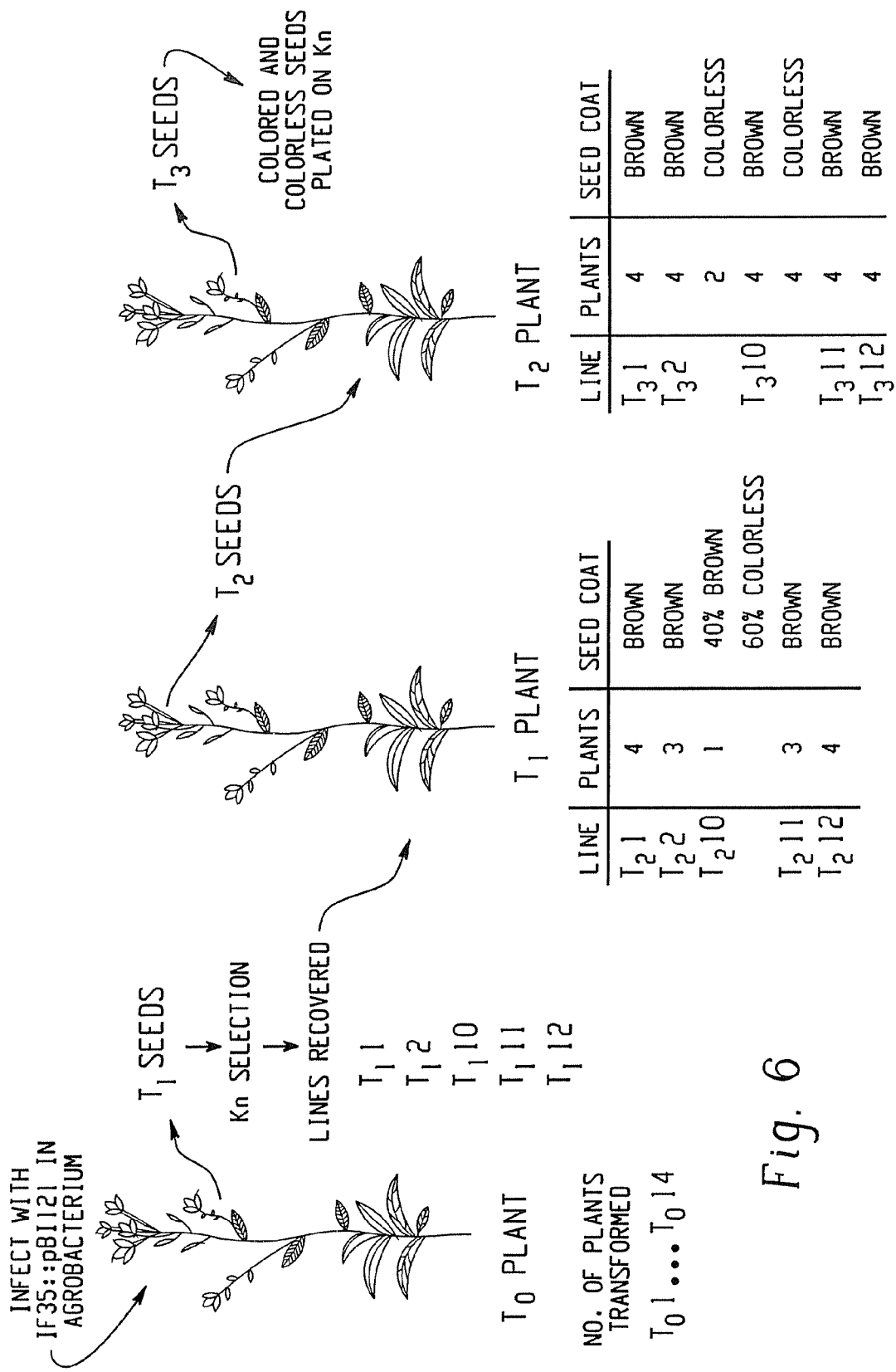
FIG. 6 shows the steps involved in obtaining transgenic *Arabidopsis* plant cells lines, plants, and seeds which comprise a transgene comprising a sequence which encodes the ZmMyb-IF35 protein operably linked to a CaMV 35S promoter.
Figure 7:
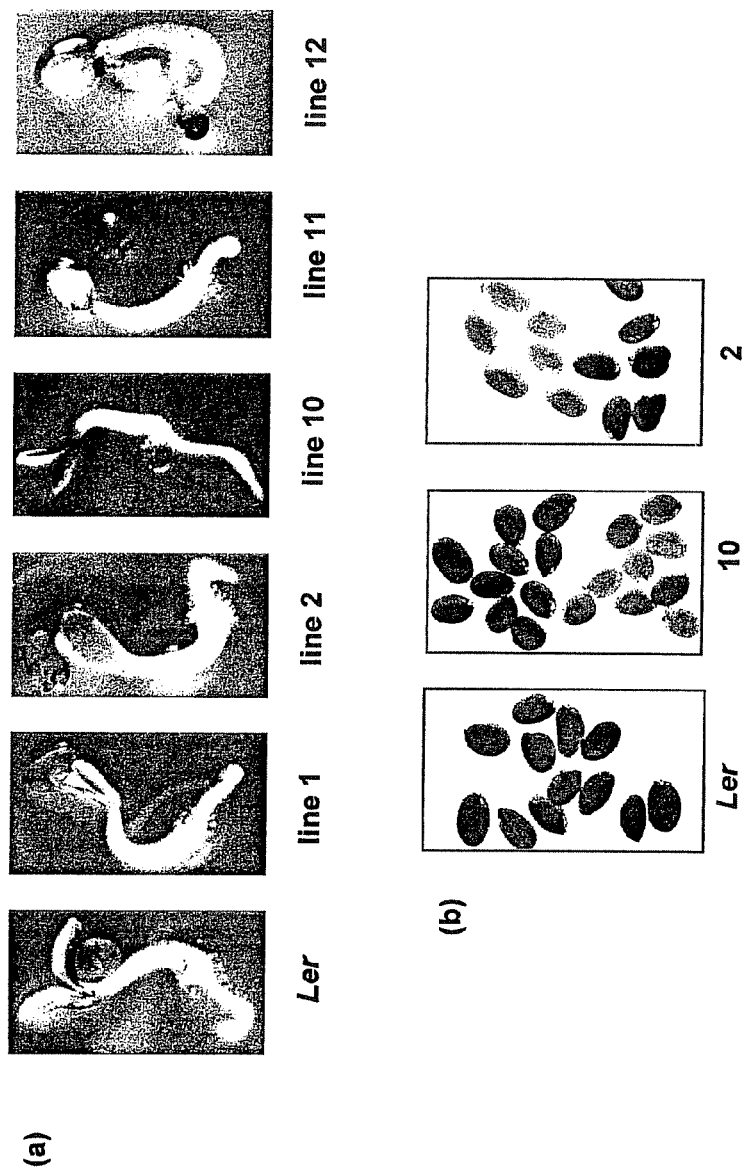
FIG. 7(*a*) shows the pigments produced in transgenic *Arabidopsis* seedlings which comprise a transgene comprising a sequence which encodes the ZmMyb-IF35 protein operably linked to a CaMV 35S promoter.

DNA constructs comprising the CaMV 35S promoter, operably linked to a cDNA encoding a transactivator protein comprising SEQ ID NO. 2, and a herbicide resistance gene were prepared using standard recombinant DNA techniques. All constructs were introduced into Arabidopsis cells via an Agrobacterium vector. Following infection, plants were regenerated from the transformed cells. (See FIG. 6.) As shown in FIG. 7(a) seedlings derived from these transformed cell lines exhibited accumulation of anthocyanin pigments near and around the cotyledons. The second generation plants derived from cell line 10 and the third generation plants derived from line 2 also exhibited colorless seed coats (See FIG. 7(b)), indicating that the expression ov ZmMyb-IF35 is interfering with the accumulation of tannins.

Example 2

DNA constructs comprising the CaMV 35S promoter, operably linked to a cDNA encoding a transactivator protein comprising SEQ ID NO. 2, and a herbicide resistance gene were prepared using standard recombinant DNA techniques. All constructs were introduced into Arabidopsis cells via an Agrobacterium vector. Following infection, plants were regenerated from the transformed cells. (See FIG. 6.) As shown in FIG. 7(a) seedlings derived from these transformed cell lines exhibited accumulation of anthocyanin pigments near and around the cotyledons. The second generation plants derived from cell line 10 and the third generation plants derived from line 2 also exhibited colorless seed coats (See FIG. 7(b)), indicating that the expression of ZmMyb-IF35 is interfering with the accumulation of tannins.

Figure 8:
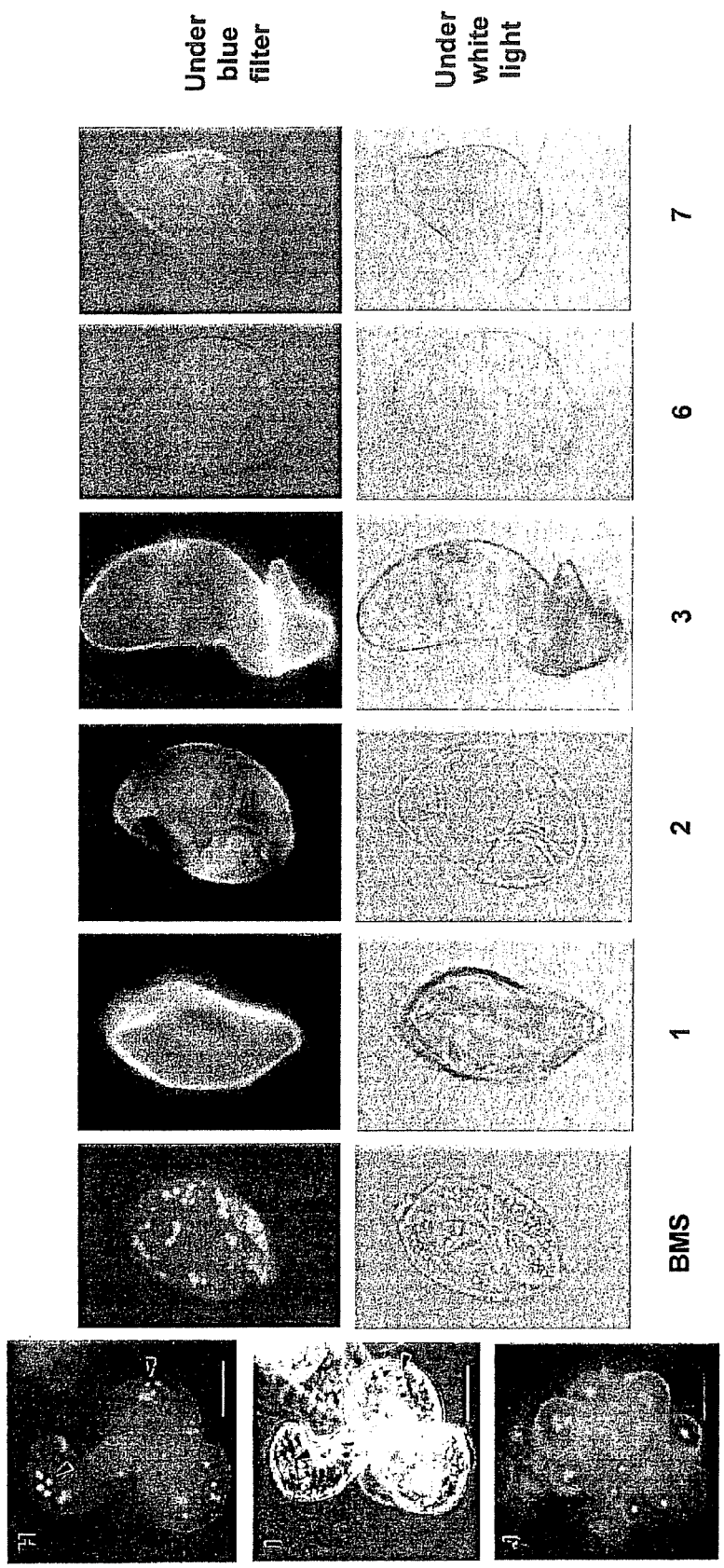
FIG. 8 shows the expression of green fluorescence in a callus of maize cells transformed with a transgene comprising a sequence which encodes the maize ZmMyb-IF35 protein operably linked to a CaMV 35S promoter.

As shown in FIG. 8, the transformed maize callus cells produced in accordance with this method exhibit green fluorescence on the cell walls, while control lines transfected with a construct containing the herbicide resistance gene but lacking a DNA which encodes the ZmMyb-IF35 protein exhibited yellow bodies in the cytoplasm.

Figure 9:
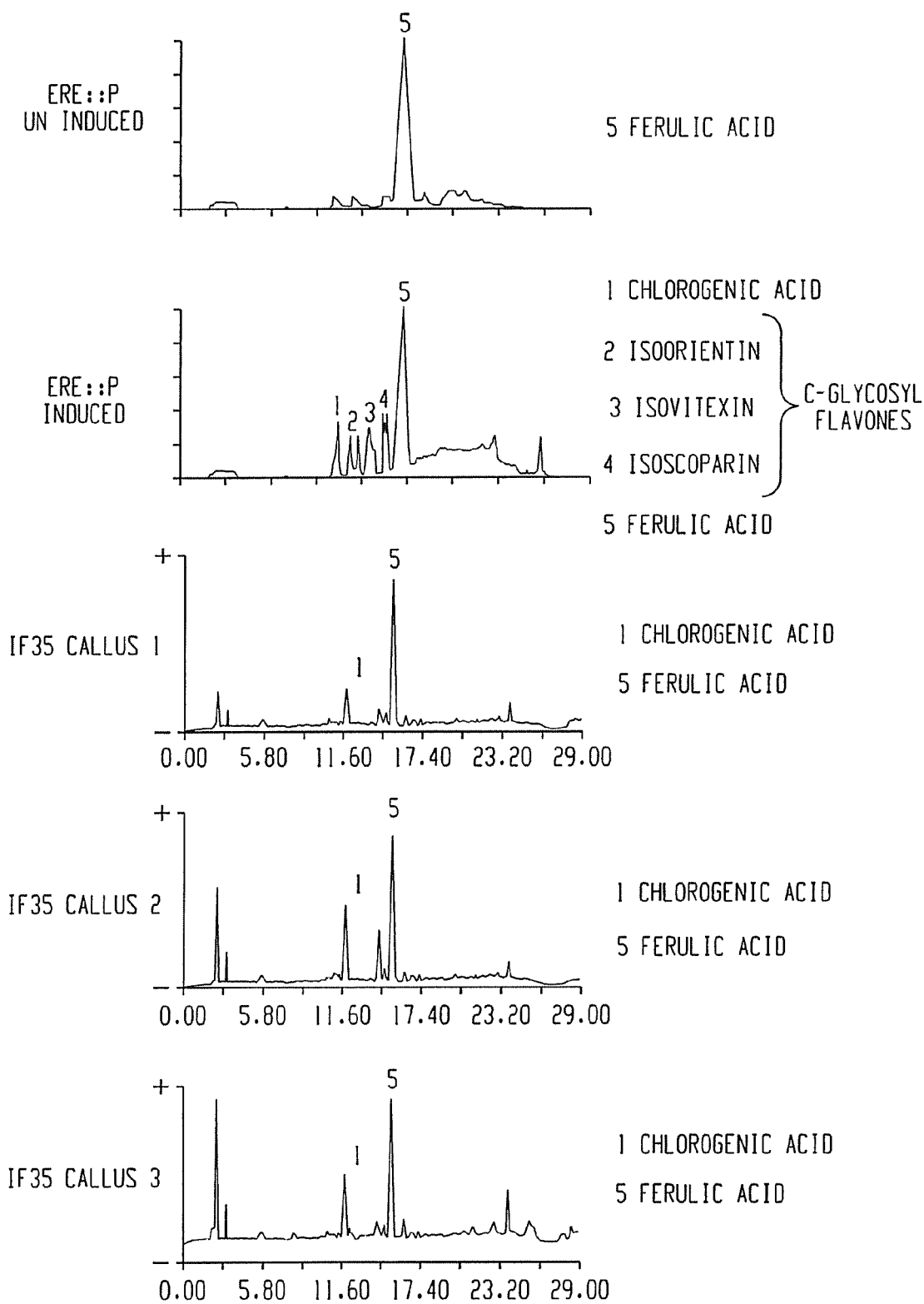
FIG. 9 shows the accumulation of ferulic acid and chlorogenic acid in a callus of maize cells transformed with a transgene comprising a sequence which encodes the maize ZmMyb-IF35 protein operably linked to a CaMV 35S promoter.

As shown if FIG. 9, the transformed maize callus cells also contained elevated levels of the phenolic compounds ferulic acid and chlorogenic acid.

What is claimed is:

1. An expression construct for preparing a plant with altered levels of one or more phenolic compounds of the phenylpropanid pathway of the plant comprising:
   a) a DNA molecule comprising a sequence which encodes an antisense RNA comprising a sequence which is complementary to at least 115 consecutive nucleotides in an RNA that encodes SEQ ID NO: 2; and
   b) a promoter for regulating transcription of said DNA molecule, said promoter being operably linked to said antisense RNA encoding sequence.

2. A method of preparing a transgenic plant containing altered levels of one or more phenolic compounds of the phenylpropanid pathway of the plant, comprising
   a) transforming a plant cell with the expression construct of claim 1; and
   b) regenerating a plant from said transformed plant cell.

3. A transgenic plant prepared by the method of claim 2.

4. An expression construct comprising an antisense DNA sequence that prevents synthesis of an endogenous ZmMyb-IF35 protein in a plant cell, operably linked to a promoter, wherein said endogenous ZmMyb-IF35 protein comprises amino acid 1 through amino acid 345 of SEQ ID NO: 2.

5. An expression construct for preparing a plant with altered levels of one or more phenolic compounds of the phenylpropanid pathway of the plant comprising
   a) a DNA molecule comprising a sequence which encodes a ZmMyb-IF35 sense RNA and a sequence which encodes a ZmMyb-IF35 antisense RNA, and a linker which links the ZmMyb-IF35 sense RNA encoding sequence to the ZmMyb-IF35 antisense RNA encoding sequence; and
   b) a promoter for regulating transcription of said DNA molecule, said promoter being operably linked to the ZmMyb-IF35 sense RNA encoding sequence and the ZmMyb-IF35 antisense RNA encoding sequence.

6. A method of preparing a transgenic plant containing altered levels of one or more phenolic compounds, comprising a) transforming a plant cell with the expression construct of claim 5; and
b) regenerating a plant from said transformed plant cell.

7. A transgenic plant prepared by the method of claim 6.

* * * * *

SEQUENCE LISTING

<160> NUMBER OF SEQ ID NOS: 2

<210> SEQ ID NO 1
<211> LENGTH: 3845

```
<212> TYPE: DNA
<213> ORGANISM: maize ZmMyb-IF-35 gene

<400> SEQUENCE: 1
tcgacccacg cgtccgcacc agcagcagag ccccgagcaa tcccttctcg cccttttcac      60
ttttcagatc cagccagcca gccagccatc ccactccgca ccgcattcct cgcagtggca     120
gagcttgcag cggtggtctc ttccccttcc tcctgtctcc tcctcgctcg atctcctctc     180
ccaagcagcg agaagcggat ggggagggcg ccgtgctgcg agaaggtggg gctgaagaag     240
gggaggtgga ccaaggagga ggacgaggtc ctggcgaggt acatcaagga gcacggggaa     300
ggatcgtgga ggtcactgcc caagaatgcc ggtacggatc gaagtggcga gtttgttata     360
ttagctagct ctgtgtgttg caataggggg gctgaggct ggttttgctg cagggctgc      420 tgcggtgcgg gaagagctgc aggctgcggt ggatcaacta cctgcgggcg gtctcaaga     480 gggggaacat ctcggaggag gaggaggaca tgatcatcaa gctccacgcc acgcttggca     540
acaggtacct gtccatgcct atctatctat ctactatctg gcattcgatt ccttcaacct     600
cgagctgctt gggccgtgtc cacagtccat cttttctctt tgattaattc ctgcgcttaa     660
tcaactccat ccatgctctg gccgcttca gggttcagag ttcttgcacg gtacgtagta     720
gggggacgaa aaaccctgtg cgctttatta tgccaccgac cgacagtggc gaatctaggt     780
ccaatttact tgatattttt ttttttctct ctctctctcc atctggtgca aagtgagaac     840
gggagggcat gtgccaagaa gctctgttcc ccccttccac tgaaagagaa ggaaccaaaa     900
tcaaatggca gaggaacacg gagttgccaa accaggccg cgcgtagatg cccctccccc     960
tcccttcaat tgttcattca gatagagcct gtttgactag tatgctatct ttgttccatc    1020 aaaaaaata tagatggttg aaatgtagtt ttagagacta gaagaggtgc ggaaaaggtc    1080
gcggttttag caatgccttc cggatgtcca gttagtgtcg tggtgcaccc gccgtcttgc    1140
cggccggcta ggtagaaacg tggtcaagac acatttcttt ctagacggag acggaagagg    1200
aggaagccgc cccccgtgt gctttcatgg acaggatggt cgagcaagca aaaaccctgc    1260
acactggacg gtcacctttg tcaatggcca ctttttgtca tggggcgagt gagtgcacgg    1320 tactttttcta cgtccgccct cgttggcctc gtgcgcgcac gtagaatgtg ccgccatcgc    1380
catggaaaag aagagggcag ccgcagcgca gggaattatt tcttcggttt ctctttcctc    1440
cgcgcctcaa tcgttggtca ttcccattgg cggattaaaa acaatcctaa gggctagttt    1500
agaaacctcg ttttcccatg agattttat tttttttaagg aaaattattc atttctctt    1560 ataaaaatag gaatccctta gaaaaatagt gttcccaaaa cactatttc taagggtttt    1620 tcgttttttcc aagataaatt agttcatttt ttttgaaaaa ttggaaattt catgaaaaa     1680 tggtgttggc aaactagtcc taaatctgca actttaataa tccttcgttc tgtcattatt    1740
agtaccccta ctcgttttag ctctgttttt ttttaatttg agatatagac ataaaaagaa    1800
cctaaattca gacgtctaaa caaattttac cgagttgcaa aatgaatgaa tcaggacccc    1860
cctaaattta gctctgctgc aggccgctgg caaggcatgt agggcagggc agtcgtttgc    1920
cacgcggtcc ggctcgctta acacgtggtt tgaatatata ttttttactc agacacgcga    1980
tagaaaaaag atgccggagt tagggagaga aaaagaaagg ggaatattcc ttgtccagcg    2040
aagagctagg ccacacccac acgatatgga ctgcactgca cgtactggga tattcggtat    2100
cctggtcacc ccggcattat ttggacaata tatatgta ggggcgggtc cgcgatccca     2160
aagtcggacg cgctacgtgt tatttggacg cctggaacct ctctcgtttc tcacgtggga    2220
```

-continued

```
ctatcgtacc cctactctac gtgtatctat atcgtgctcg tcacatgaca cgcacaccac    2280
ttgtcggtag acagacatcg gcccccaaga accgaagtgc tacgccctct ccccgaccac    2340
tgcacactgg tgcctgtcgc actgtatgag agatgcgtgg ctcggcaaat tcggagcgga    2400
ttaatgtcgt caccaagaaa ctagaaacca cttgcgttcg tcacctttca tggaccccag    2460
cagctgcagc aatcctgcca acggaaacgc gcgcacatgg tgcattagtt cgcgtggacg    2520
ccgctgcgat ccttcatttc gtttcgttta tttactatac tcgcgcgcgc cgcagctagc    2580
tatggttgtt agatcaccag cacgcgtatt gattgccaca tgtgcctgcc gcctggactg    2640
gacctgcagt gcagctcctg tcctgtgcac gcctctccct gctgttctta gtctcatcaa    2700
cctcaagttt cattcttctt ttcttctccc cgcaggtggt ccctgatcgc cggtcacttg    2760
cccggtcgaa cagacaacga gatcaaaaac tactggaact cgcacctgag caggcgggcg    2820
gccgacttcc gcgacggcgt cgtcgtcgac atcgacctca gcaagctgcc cggcggcggg    2880
aaacggcgcg gcggccgggc cagccggggc gccgtcgtgg ccgcggccaa ggagaagaag    2940
gccaaggaga aggacgacag gggcaatagc aaggtcgcag aagcggagca gcagctcagg    3000
gacacggagg acgacgacgg cggcagcgtc tccacgccga ggcctcagtc tgatgactgc    3060
ggcaccgccc agagcgaaga ggagcaagcg caggccagcg ccagcggcct gacatccgat    3120
gggcatgggc ccgaggagga ggaggaggag gacccgctgg ctctgagcga ggagatggtg    3180
agtgcgcttc tggccccgga aagcccaaag ctggaggtgg ccccgatgg ctcgtgcatg    3240 gacagctaca gtgccctcc gtcaggggaa agcggctgtg gtccagtgg gccttctggc    3300 gacgtggccc aggacctgga cctagacgac gacaaggcca tcatggactg ggacttgatg    3360
gggctgggac atctcgaccc gccggtgaca tgtgggacca gctggtgtgg gactacgacg    3420
aaacgttggt cacggaaccg gaaggagggg aggaagggca ccagcagcag gacgatgtca    3480
tgtcagacct cttcttcctg gacaatctct aggaggtgcg aggatagcat gggcatggct    3540
gccgtgatgc tttatgcttt ttaatttgat ccggtacttg taggttttg ggtgtgttca    3600 gttcaaagat gagtggcggt gtcagagacg agataagggg agtgctccag tgacatcttt    3660
gtttgctggc cggatctcac gaacccgtag aatggcaaga atgtagaaaa ataagcacgc    3720
aatatcactt ggaaacccttt catcagtaga gcctgtctaa catctacaga cggagaaatg    3780
caaaaaaaaa aaaaaaggt tgctggggtt ataaaaaaaa aaaaaaaaa aaaaaaaaa       3840 aaaaa                                                              3845
```

<210> SEQ ID NO 2
<211> LENGTH: 363
<212> TYPE: PRT
<213> ORGANISM: maize ZmMyb-IF-35 protein

<400> SEQUENCE: 2

```
Met Gly Arg Ala Pro Cys Cys Glu Lys Val Gly Leu Lys Lys Gly Arg
 1               5                  10                  15

Trp Thr Lys Glu Glu Asp Glu Val Leu Ala Arg Tyr Ile Lys Glu His
             20                  25                  30

Gly Glu Gly Ser Trp Arg Ser Leu Pro Lys Asn Ala Gly Leu Leu Arg
         35                  40                  45

Cys Gly Lys Ser Cys Arg Leu Arg Trp Ile Asn Tyr Leu Arg Ala Gly
     50                  55                  60

Leu Lys Arg Gly Asn Ile Ser Glu Glu Glu Asp Met Ile Ile Lys
 65                  70                  75                  80
```

-continued

```
Leu His Ala Thr Leu Gly Asn Arg Trp Ser Leu Ile Ala Gly His Leu
             85                  90                  95
Pro Gly Arg Thr Asp Asn Glu Ile Lys Asn Tyr Trp Asn Ser His Leu
            100                 105                 110
Ser Arg Arg Ala Ala Asp Phe Arg Asp Gly Val Val Val Asp Ile Asp
            115                 120                 125
Leu Ser Lys Leu Pro Gly Gly Gly Lys Arg Arg Gly Gly Arg Ala Ser
            130                 135                 140
Arg Gly Ala Val Val Ala Ala Ala Lys Glu Lys Lys Ala Lys Glu Lys
145                 150                 155                 160
Asp Asp Arg Gly Asn Ser Lys Val Ala Glu Ala Glu Gln Gln Leu Arg
                165                 170                 175
Asp Thr Glu Asp Asp Asp Gly Gly Ser Val Ser Thr Pro Arg Pro Gln
            180                 185                 190
Ser Asp Asp Cys Gly Thr Ala Gln Ser Glu Glu Glu Gln Ala Gln Ala
            195                 200                 205
Ser Ala Ser Gly Leu Thr Ser Asp Gly His Gly Pro Glu Glu Glu Glu
            210                 215                 220
Glu Glu Asp Pro Leu Ala Leu Ser Glu Glu Met Val Ser Ala Leu Leu
225                 230                 235                 240
Ala Pro Glu Ser Pro Lys Leu Glu Val Gly Pro Asp Gly Ser Cys Met
            245                 250                 255
Asp Ser Tyr Ser Gly Pro Pro Ser Gly Glu Ser Gly Cys Gly Ser Ser
            260                 265                 270
Gly Pro Ser Gly Asp Val Ala Gln Asp Leu Asp Leu Asp Asp Asp Lys
            275                 280                 285
Ala Ile Met Asp Trp Asp Leu Met Gly Leu Gly His Leu Asp Pro Pro
290                 295                 300
Val Thr Cys Gly Thr Ser Trp Cys Gly Thr Thr Thr Lys Arg Trp Ser
305                 310                 315                 320
Arg Asn Arg Lys Glu Gly Arg Lys Gly Thr Ser Ser Arg Thr Met Ser
            325                 330                 335
Cys Gln Thr Ser Ser Ser Trp Thr Ile Ser Arg Arg Cys Glu Asp Ser
            340                 345                 350
Met Gly Met Ala Ala Val Met Leu Tyr Ala Phe
            355                 360
```